(12) United States Patent
Bondhus et al.

(10) Patent No.: US 10,092,748 B2
(45) Date of Patent: Oct. 9, 2018

(54) STRAIN RELIEF LOOP HOLDERS FOR MEDICAL LEADS AND SYSTEMS

(71) Applicant: MEDTRONIC, INC., Minneapolis, MN (US)

(72) Inventors: Spencer M. Bondhus, Columbia Heights, MN (US); Bryan D. Stem, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 15/426,051

(22) Filed: Feb. 6, 2017

(65) Prior Publication Data

US 2017/0182313 A1 Jun. 29, 2017

Related U.S. Application Data

(63) Continuation of application No. 14/395,195, filed as application No. PCT/US2013/023643 on Jan. 29, 2013, now Pat. No. 9,561,364.

(60) Provisional application No. 61/635,784, filed on Apr. 19, 2012.

(51) Int. Cl.
*A61N 1/08* (2006.01)
*A61N 1/05* (2006.01)

(52) U.S. Cl.
CPC .............. *A61N 1/08* (2013.01); *A61N 1/05* (2013.01); *A61N 1/056* (2013.01); *A61N 1/086* (2017.08); *A61N 2001/0582* (2013.01)

(58) Field of Classification Search
CPC . A61N 1/08; A61N 1/05; A61N 1/056; A61N 1/086; A61N 2001/0582
USPC .......................................... 607/115, 116, 117
See application file for complete search history.

(56) References Cited

U.S. PATENT DOCUMENTS

| | | | | |
|---|---|---|---|---|
| 5,376,108 A | * | 12/1994 | Collins | A61N 1/056 604/174 |
| 6,471,676 B1 | * | 10/2002 | DeLegge | A61M 25/0113 604/175 |
| 8,483,845 B2 | * | 7/2013 | Sage | A61N 1/0558 607/117 |

* cited by examiner

*Primary Examiner* — Carl H Layno
*Assistant Examiner* — Erin M Piateski
(74) *Attorney, Agent, or Firm* — Withers & Keys, LLC

(57) ABSTRACT

Strain relief loop holders maintain the strain relief loop formed in a lead while also addressing the excessive heating at the point in the loop where the medical lead intersects with itself. The strain relief loop includes a body section that the medical lead passes through where the intersection occurs. The body section may be a thermal non-conductor and isolate from excessive heating at the intersection point or may be a thermal conductor and distribute the excessive heating. The strain relief loop may include features such as arms or a coil extending from the body segment with arm segments at the ends of the arms defining lead passageways that assist in maintaining the strain relief loop. The body segment may have a single lead passageway where the intersection point occurs or may have multiple lead passageways. The body itself may house the loop by forming a loop or a capsule.

20 Claims, 19 Drawing Sheets

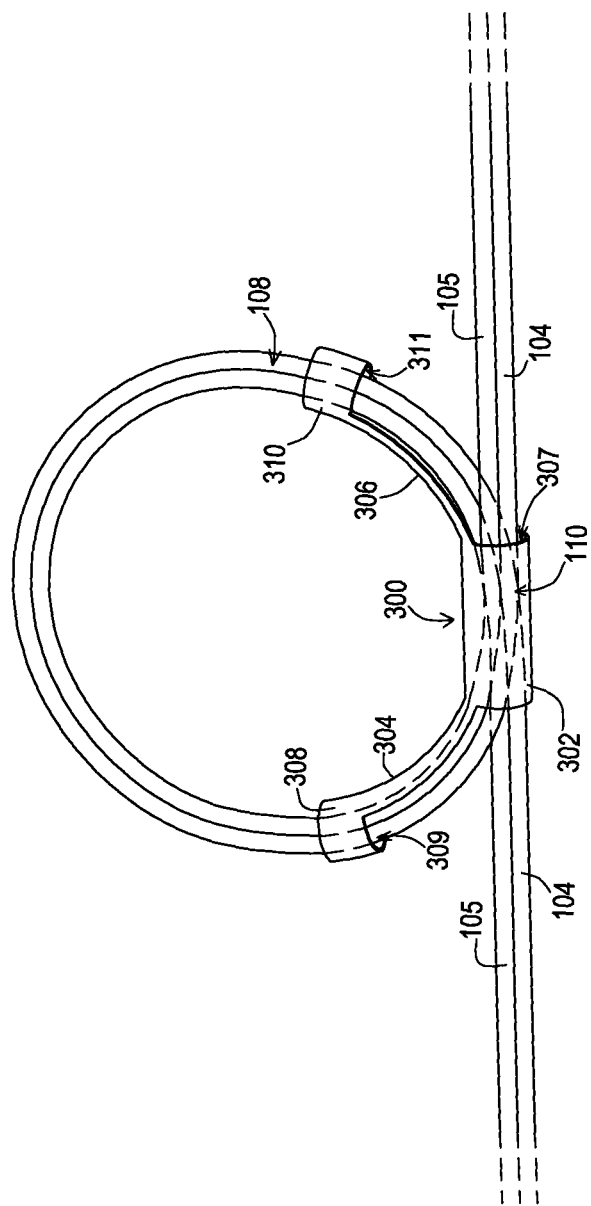

STRAIN RELIEF LOOP HOLDERS FOR MEDICAL LEADS AND SYSTEMS

RELATED PRIOR APPLICATIONS

This application is a continuation of U.S. patent application Ser. No. 14/395,195, which was filed on Oct. 17, 2014, which issued as U.S. Pat. No. 9,561,364 on Feb. 7, 2017, which claims the benefit of PCT Application PCT/US2013/023643, filed on Jan. 29, 2013, which claims priority to U.S. Provisional Application No. 61/635,784, filed on Apr. 19, 2012.

TECHNICAL FIELD

Embodiments are related to strain relief loops for medical leads. More particularly, embodiments are related to strain relief loop holders that establish a strain relief loop for medical leads.

BACKGROUND

Medical leads provide electrical stimulation from a medical device to a target site within a body of a patient. The medical device is typically implanted or otherwise installed on the body in an accessible area at some distance from the target site, and the medical lead is routed to the target site either through a percutaneous procedure or by surgical implantation depending upon the type and size of the medical lead being implanted.

Because the medical lead extends some distance between the medical device and the target site within the body, the medical lead is subject to forces imposed by movements of the patient. In particular, the medical lead may be subjected to strain. To address the strain, the medical lead may be routed by creating a loop that relieves the strain by the loop making available an additional length of the lead.

While this strain relief loop does relieve the strain, an issue occurs when the patient is subjected to radiofrequency (RF) electromagnetic energy in excess of the ambient, such as when having a magnetic resonance imaging (MRI) scan. The metal conductors within the lead, such as filars and/or a shield, have current induced by the RF energy. This induced current can produce heating within the medical lead but the heating is typically distributed over a length of an MRI conditionally safe lead and is not troublesome. However, with a strain relief loop, the heating tends to be more intense at the intersection point on the loop where the medical lead loops back onto itself. This more intense heating at the intersection point may produce discomfort or injury for the patient.

SUMMARY

Embodiments address issues such as these and others by providing strain relief loop holders for medical leads and systems. The embodiments provide a body section that covers the intersection point. Some embodiments provide one or more passageways that the lead passes through when forming the strain relief loop. The body section insulates the tissue from the intersection point when constructed of a thermal non-conductor and distributes the heat over a larger amount of tissue to prevent excessive tissue heating when constructed of a thermal conductor. The embodiments may further provide features such as arms or a coil extending from the body section to further define passageways that the medical lead passes through to establish and maintain the strain relief loop. Furthermore, the embodiments may provide for a body that takes the form of a loop or a capsule.

Embodiments provide a strain relief loop holder that includes a body segment defining at least one passageway. A first arm extends from a first end of the body segment. A first arm segment is located at an end of the first arm opposite the body segment, the first arm segment defining a first arm passageway. A second arm extends from a second end of the body segment. A second arm segment is located at the end of the second arm opposite the body segment, the second arm segment defining a second arm passageway.

Embodiments provide a medical lead strain relief system that includes a strain relief loop holder. The strain relief loop holder includes a body segment defining at least one passageway. A first arm extends from a first end of the body segment. A first arm segment is located at an end of the first arm opposite the body segment, the first arm segment defining a first arm passageway. A second arm extends from a second end of the body segment. A second arm segment is located at the end of the second arm opposite the body segment, the second arm segment defining a second arm passageway. The medical lead strain relief system further includes a medical lead that passes through the first arm passageway and the second arm passageway, the medical lead forming a loop by passing through and intersecting within the body segment.

Embodiments provide a medical system that includes a strain relief loop holder. The strain relief holder includes a body segment defining at least one passageway. A first arm extends from a first end of the body segment. A first arm segment is located at an end of the first arm opposite the body segment, the first arm segment defining a first arm passageway. A second arm extends from a second end of the body segment. A second arm segment is located at the end of the second arm opposite the body segment, the second arm segment defining a second arm passageway. The medical system further includes a medical lead that passes through the first arm passageway and the second arm passageway, the medical lead forming a loop by passing through and intersecting within the body segment. Additionally, the medical system includes a medical device with the medical lead being coupled to the medical device.

Embodiments provide a medical lead strain relief system that includes a strain relief loop holder comprising a body defining at least one passageway, the body defining at least one entry to the at least one passageway. The medical lead strain relief system further includes a medical lead that enters and exits the at least one passageway of the body through the at least one entry, the medical lead forming a loop by loosely passing through and intersecting within the body, the at least one passageway being sized larger than the medical lead to allow the medical lead to move unrestricted axially through the at least one lead passageway while being looped loosely through the at least one lead passageway.

DESCRIPTION OF THE DRAWINGS

FIG. 3AA shows the first example of the medical lead strain relief system but with two leads present.

DETAILED DESCRIPTION

Embodiments provide strain relief holders for medical leads to provide protection from excessive heating during exposure to RF energy while also maintaining the strain relief loop. The embodiments include a body section with a passageway that the medical lead passes through and intersects within so that the heating occurs within the body section. In some embodiments, the body section may be a thermal non-conductor and insulates the tissue from the excessive heating. In other embodiments, the body section may be a thermal conductor that distributes the heating over a larger surface area and hence a larger amount of tissue to prevent excessive heating.

Figure 1:
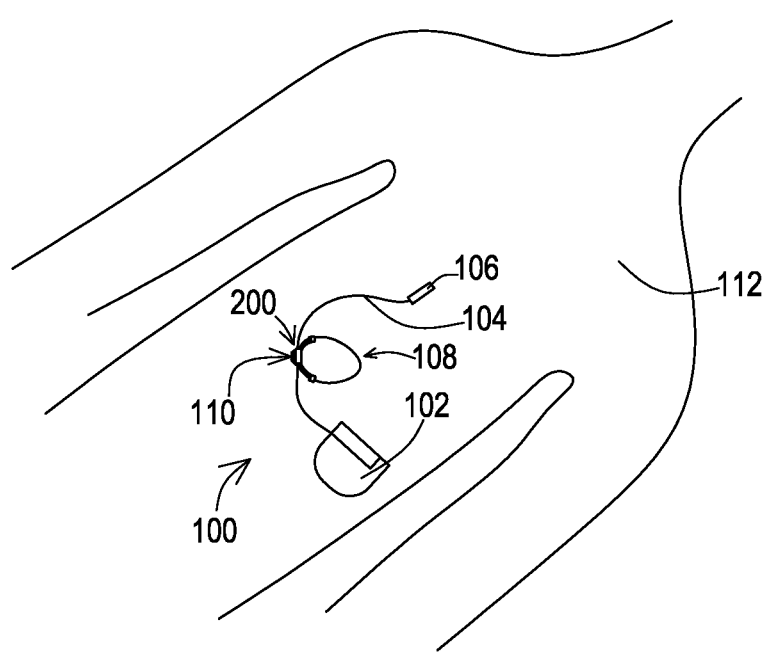
FIG. 1 shows an example of a medical system environment where a strain relief loop is created for a medical lead.

FIG. 1 shows a body 112 of a patient who has a medical system 100 implanted for providing stimulation therapy. The medical system 100 includes a medical device 102 that provides stimulation signals. A medical lead 104 is connected to the medical device 102 to deliver the stimulation signals to a distal end where electrodes are present. In this case, the medical lead 104 is a surgically implanted lead with a paddle 106 housing the electrodes for stimulation to the spine.

The medical lead 104 is routed so that a strain relief loop 108 at a location between the proximal end at the medical device 102 and the distal end at the paddle 106. The strain relief loop 108 is assisted in this example by an embodiment of a strain relief holder 200. The strain relief holder 200 holds the lead in the strain relief loop configuration while also protecting the body 112 from heating generated at the intersection point 110 when exposed to RF energy. By maintaining the strain relief loop, an added benefit is that the excessive heating occurring at the intersection point 110 results in lower heating at the target site where the paddle 106 is located.

Figure 2A:
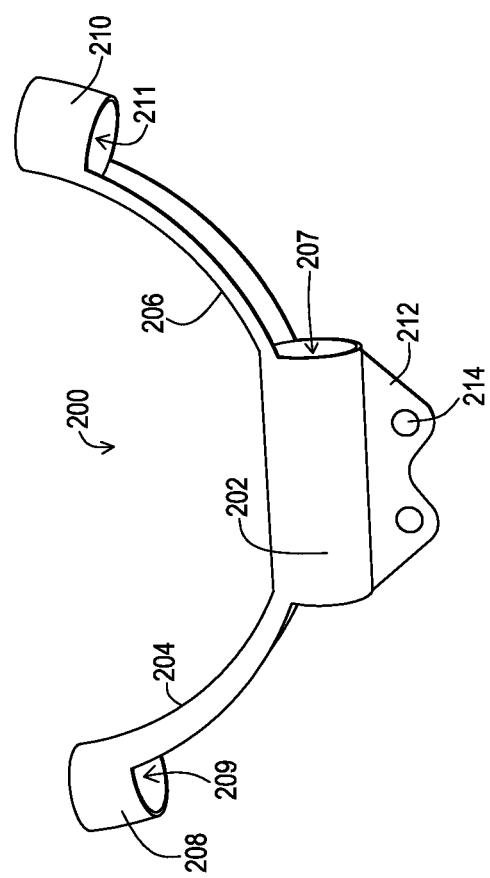
FIG. 2A shows a first example of a strain relief loop holder with a single passageway through a body section.

The strain relief loop holder 200 of this example is shown in FIG. 2A. In this embodiment, the strain relief loop holder 200 includes a body section 202 that defines an entry to and a corresponding lead passageway 207. A first arm 204 extends from the body section 202 on a first end and terminates at a first arm section 208 that defines a lead passageway 209. A second arm 206 extends from the body section 202 on a second end and terminates at a second arm section 210 that defines a lead passageway 211. In this particular example, the first arm 204 and the second arm 206 form an arc even when the medical lead 104 is not present. In other embodiments, the first and second arms 204, 206 may be linear when the lead 104 is not installed as shown in FIG. 2C discussed below but upon looping the medical lead 104 through the strain relief holder 200, the first and second arms 204, 206 attain the arc as shown.

In forming the strain relief loop, the medical lead 104 passes through the arm segments 208, 210 and then intersects itself within the body section 202. Because the medical lead 104 passes through each arm segment 208, 210 only once but passes through the body section 202 twice to create the intersection point, the lead passageway 207 of the body segment 202 may have a larger diameter than the diameter of the arm segments 208, 210. The diameters may be sized so that the medical lead 104 is able to move axially so that the strain relief function is preserved.

The strain relief holder 200 may be constructed of various materials. For instance, the strain relief holder 200 may be constructed of a thermal non-conductor such as a biocompatible polymer, examples including silicone, polyurethane, PEEK, polysulfones, and the like. In that case, the body section 202 insulates the body tissue from heating occurring at an intersection point of the loop within the body section 202. The strain relief holder 200 may instead be constructed of a thermal conductor such as a biocompatible metal, examples including MP35N, titanium, and the like. In that case, the body section 202 distributes the heating throughout the strain relief holder 200, including across all of the body section 202, the arms 204, 206, and the arm sections 208, 210.

This particular example also includes an integral anchor tab 212. The anchor tab 212 provides one or more suture holes 214. These holes 214 allow a surgeon implanting the lead to suture the anchor tab 212, and hence the strain relief loop holder 200 and the medical lead 104 within it, to a particular location within the body 112.

Figure 2B:
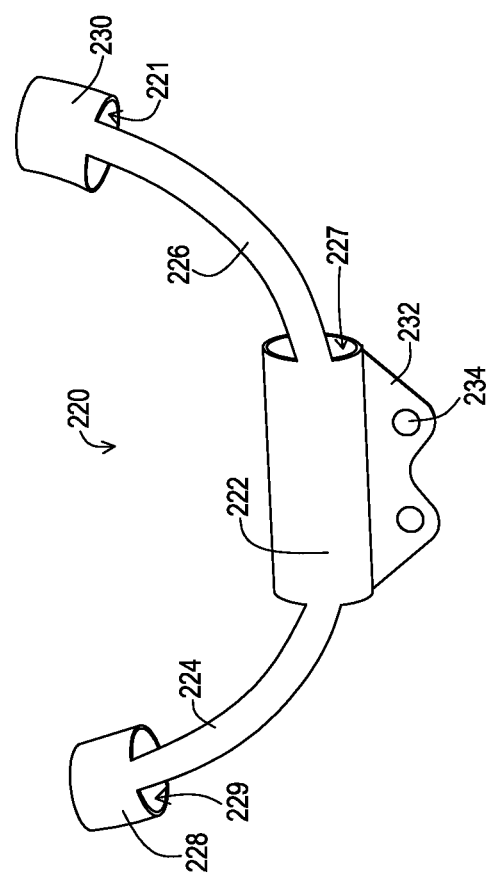
FIG. 2B shows a second example of a strain relief loop holder with a single passageway through a body section.
Figure 2C:
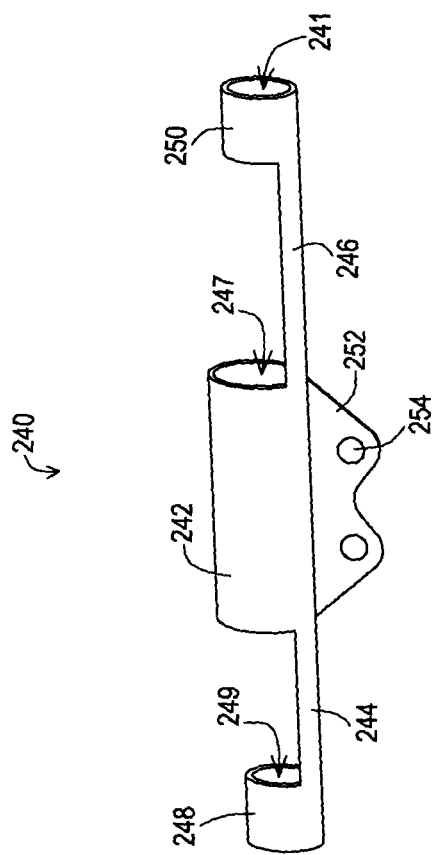
FIG. 2C shows a third example of a strain relief loop holder with a single passageway through a body section.

FIG. 2B shows another example of a medical lead strain relief loop holder 220 that may be used in the system of FIG. 1. This example is similar to that of FIG. 2A except that the arms 224 and 226 are positioned on the side of the loop 108 as opposed to the arms 204 and 206 being on the inside of the loop 108. The arm sections 228 and 230 define lead passageways 229 and 221 while the body section 222 defines a lead passageway 227. This example also includes the integral anchor 232 with suture holes 234.

FIG. 2C shows another example of a medical lead strain relief loop holder 240 that may be used in the system of FIG. 1. This example is similar to that of FIG. 2A except that the arms 224 and 226 do not have pre-formed arcs. Instead, the arms 224 and 226 are constructed of an elastic material such as polyurethane or silicone that allows them to achieve an arc upon passing the lead 104 through the lead passageway 247 of the body 242 and through the passageways 241, 249 of the arm sections 248, 250. This example also includes the integral anchor 252 with suture holes 254.

Figure 3A:
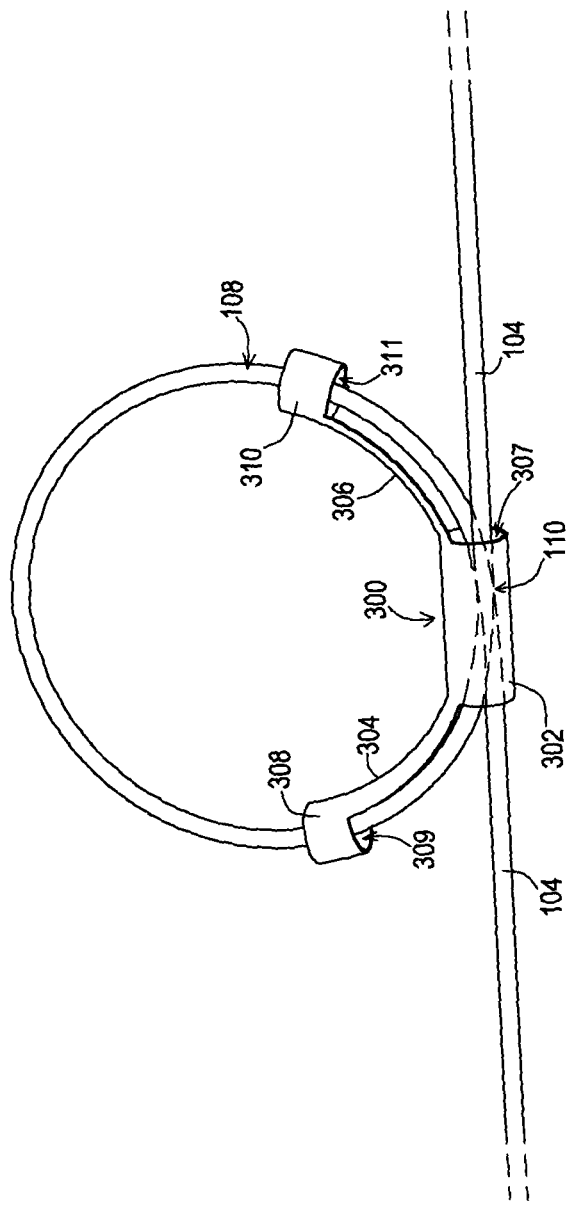
FIG. 3A shows a first example of a medical lead strain relief system including a fourth example of a strain relief loop holder.

FIG. 3A shows a medical lead strain relief system including a similar strain relief loop holder 300 as that shown in FIG. 2A that may be used in the system of FIG. 1. FIG. 3AA shows the same example but with two medical leads 104, 105 being looped through the holder 300. It will be appreciated that such a system may instead be designed to accommodate any number of leads passing through. However, this example in FIG. 3AA of two leads 104, 105 passing through a same strain relief loop holder 300 is particularly convenient where a single paddle 106 has two medical lead bodies that interconnect the paddle 106 to the medical device 102. The intersection point 110 for lead 104 in FIG. 3A and for each lead 104, 105 in FIG. 3AA can be seen within a body section 302, where the medical leads 104, 105 pass through a lead passageway 307. In forming two adjacent strain relief loops 108 of FIG. 3AA, the medical leads 104, 105 pass through a lead passageway 311 of an arm section 310 as well as a lead passageway 309 of an arm section 308. The arm sections 308 and 310 are joined to the body section 302 by arms 304 and 306.

Figure 3B:
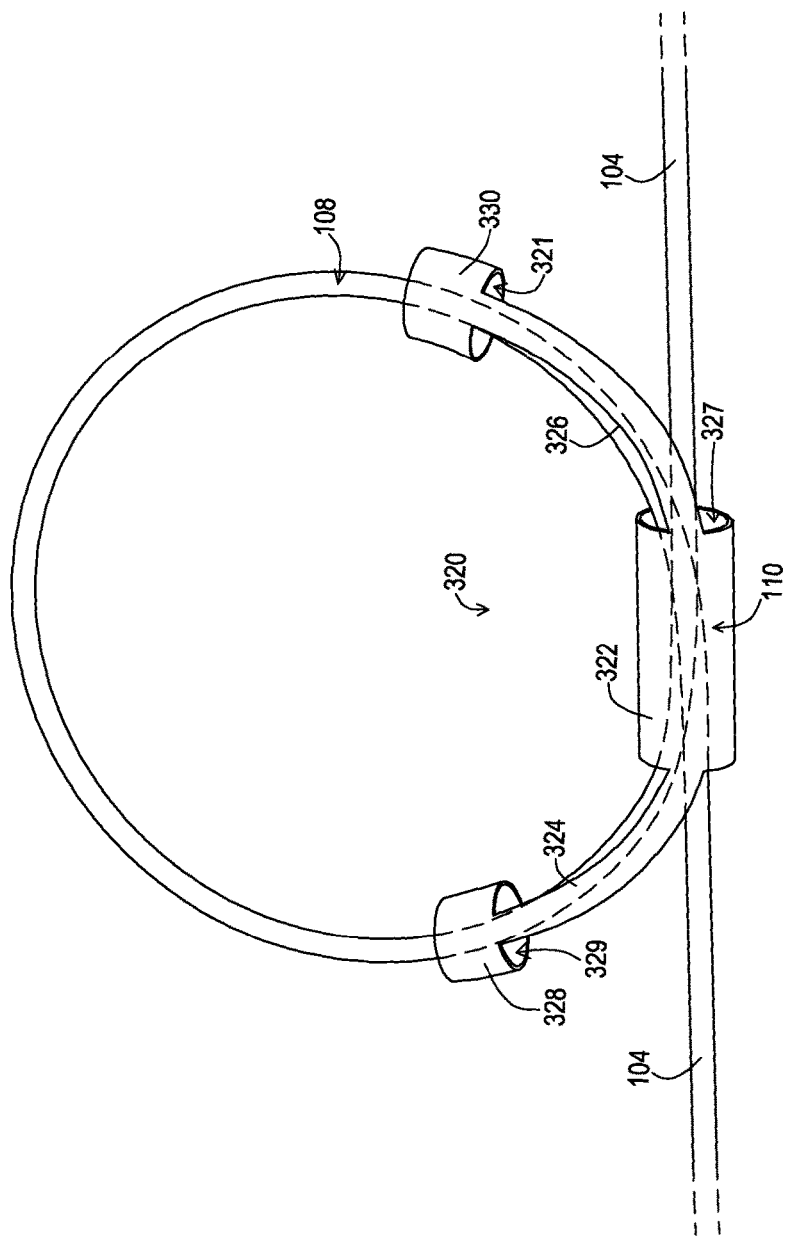
FIG. 3B shows a second example of a medical lead strain relief system including a fifth example of a strain relief loop holder.

FIG. 3B shows another example of a medical lead strain relief loop holder 320 that may be used in the system of FIG. 1. This example is similar to that of FIG. 3A except that the arms 324 and 326 are positioned on the side of the loop 108 as in the example of FIG. 2B as opposed to the arms 304 and 306 being on the inside of the loop 108. The arm sections 328 and 330 define lead passageways 329 and 321 while the body section 322 defines a lead passageway 327.

Figure 4:
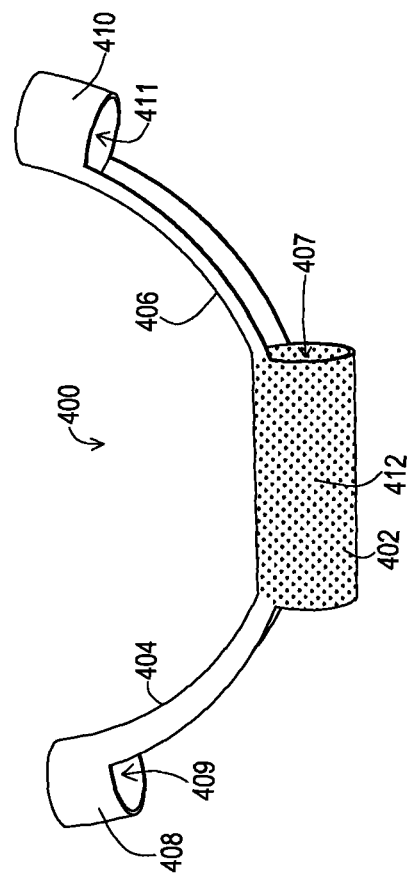
FIG. 4 shows a sixth example of a strain relief loop holder having conductive dopant.

FIG. 4 shows another example of a strain relief holder 400 that may be used in the system of FIG. 1. Like the prior examples, the strain relief holder 400 includes a body section 402 defining a passageway 407, arms 404, 406 extending from the body section 402, and arm sections 408, 410 defining lead passageways 409, 411. However, in this example, the body section 402 which is constructed of a thermal non-conductor is also doped with a thermally and/or electrically conductive material 412. The conductive material 412 may be thermally conductive to facilitate heat dissipation, such as diamond dust where electrical conductivity is not desired. The conductive material 412 may additionally or alternatively be electrically conductive to alter the transmission-line characteristics at the intersection point 110. Examples of such an electrically conductive dopant material include tantalum or plantinum. The dopant conductive material 412 may further enhance the ability of the strain relief loop holder 400 to reduce heating at the electrodes on the distal end of the lead 104. The dopant conductive material 412 may be included in the remainder of the strain relief holder 400 as well. It will be appreciated that the dopant 412 may be included within all of the various strain relief loop holders disclosed herein.

Figure 5:
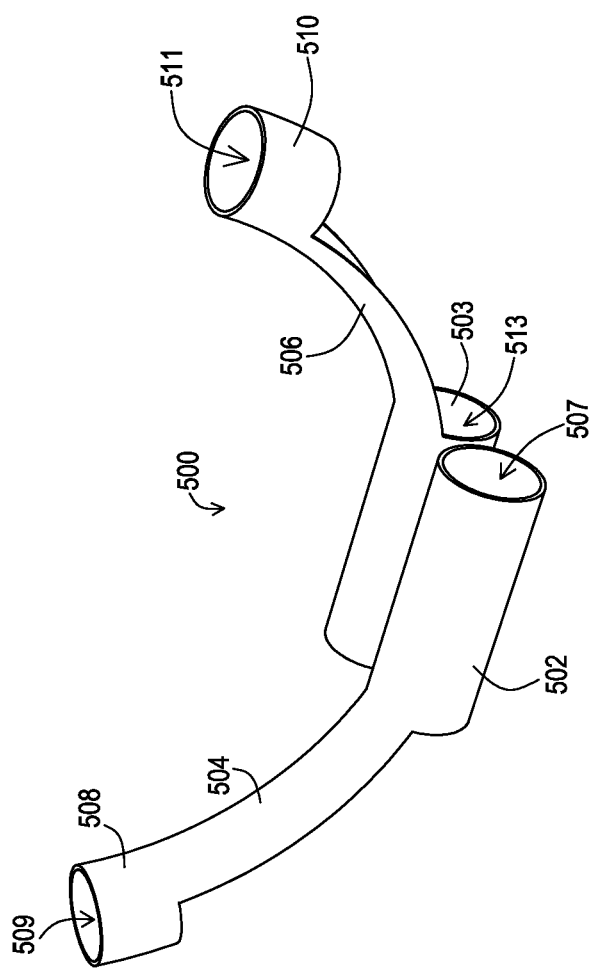
FIG. 5 shows a seventh example of a strain relief loop holder having two passageways within a body section.

FIG. 5 shows another example of a strain relief loop holder 500 that may be used in the system of FIG. 1. The strain relief loop holder 500 includes two adjacent passageways 507, 513 established by a body section 502 that includes an extra barrel 503 defining the extra passageway 513. In this example, the arm 504 extends from the body segment 502 and more particularly from the lead passageway 507. The arm 506 extends from the body segment 502 and more particularly from the extra lead passageway 513 defined by the extra barrel 503 of the body segment 502. In this example, an arm segment 508 defines a lead passageway 509 that is aligned with the lead passageway 507 while the arm segment 510 defines a lead passageway 511 that is aligned with the lead passageway 513.

Figure 6:
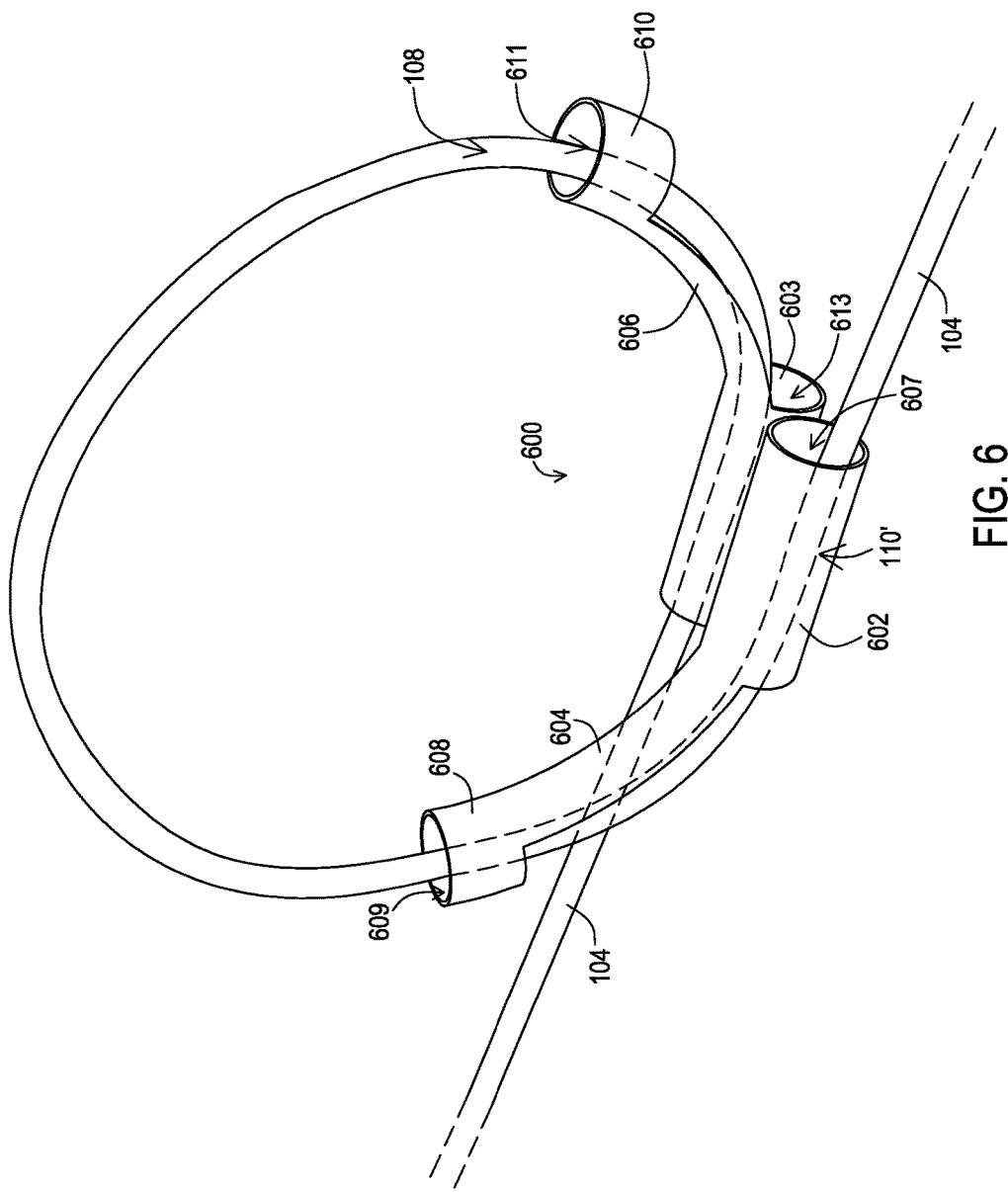
FIG. 6 shows a third example of a medical lead strain relief system including the seventh example of the strain relief loop holder.

FIG. 6 shows a medical lead strain relief system that may be used in the system of FIG. 1 and that includes the medical lead 104 looping through a strain relief loop holder 600 like that of FIG. 5. The medical lead 104 passes through a lead passageway 613 defined by the extra barrel 603, then loops through a lead passageway 611 of an arm segment 610 of an arm 606 extending from the extra barrel 603. The medical lead 104 loops through a lead passageway 609 of an arm section 608 of an arm 604 extending from the body section 602.

In this embodiment of the strain relief holder 600, the intersection point 110' differs in that the medical lead 104 does not directly contact itself. Instead, the medical lead 104 is separated from itself at the intersection point 110' passing through separate lead passageways 607, 613 of the body segment 602. This separation may reduce the degree of excessive heating at the intersection point 110'. Meanwhile, in embodiments where the body segment 602 is thermally non-conductive, the body segment 602 continues to isolate the excess heating from the body 112. For embodiments where the body segment 602 is thermally conductive, the body segment 602 continues to distribute the heating of the intersection point 110' over a larger amount of tissue.

Figure 7:
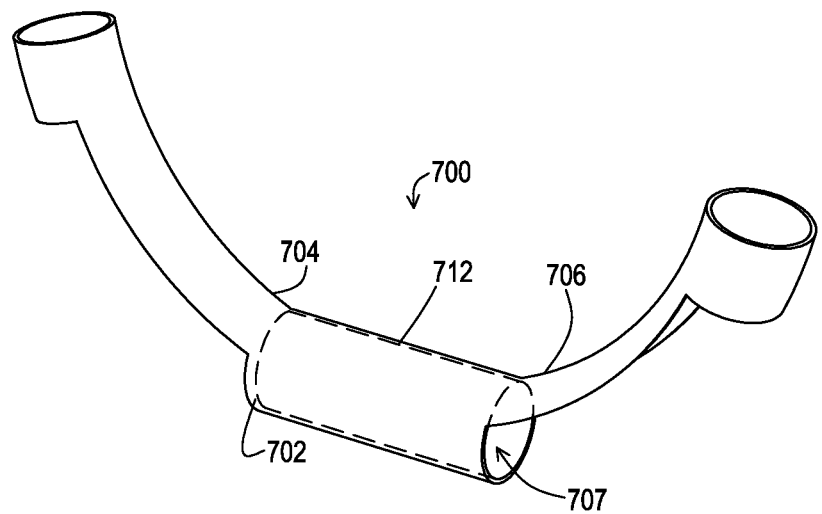
FIG. 7 shows an eighth example of a strain relief loop holder having a metal sleeve within the body section.

FIG. 7 shows another example of a strain relief loop holder 700 that may be used in the system of FIG. 1. The arms 704, 706 are abbreviated and arm segments are omitted from this figure for purposes of illustration of the perspective view. In this example, a body section 702 is constructed of a thermal non-conductor such as a polymer. However, a metal insert 712 such as a metal sleeve is embedded within the body section such that the medical lead passes through the metal insert 712 when passing through the passageway 707. This metal insert 712 enhances the benefit from heating at the intersection point within the body section 702 which further reduces the heating at the electrodes on the distal end of the medical lead 104. Examples of materials for the metal sleeve 712 include titanium, MP35N, and the like.

Figure 8:
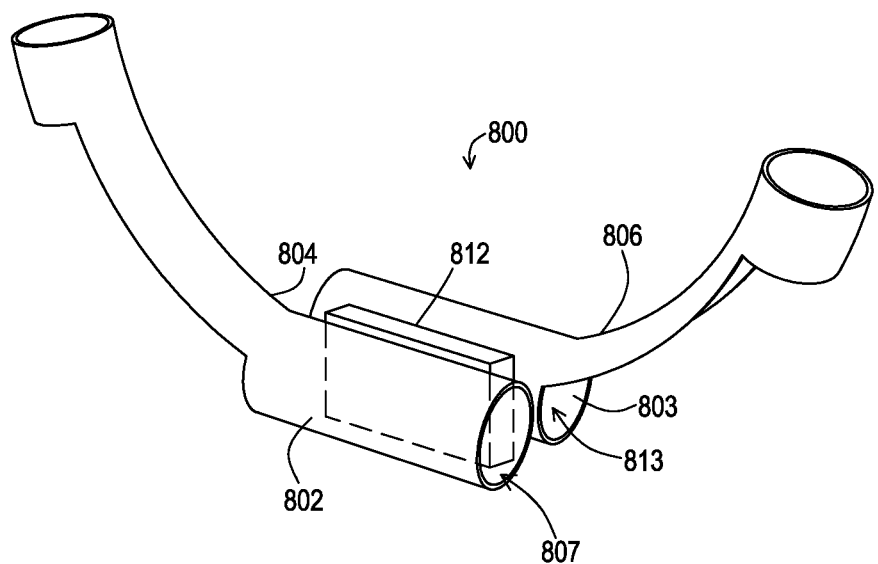
FIG. 8 shows a ninth example of a strain relief loop holder having two passageways within the body section with a metal body between the two passageways.

FIG. 8 shows another example of a strain relief loop holder 800 that may be used in the system of FIG. 1. The arms 804, 806 are abbreviated and arm segments are omitted from this figure for purposes of illustration of the perspective view. In this example, a body section 802 including an extra barrel 803 is constructed of a thermal non-conductor such as a polymer. However, a metal body 812 is embedded within the body section 802 between the two barrels such that the medical lead 104 passes through the lead passageways 807, 813 and the metal body 812 is present between the passes of the medical lead 104 at the intersection point. This metal body 812 also enhances the benefit from heating at the intersection point within the body section 802 which further reduces the heating at the electrodes on the distal end of the medical lead 104. Examples of materials for the metal body 812 include titanium, MP35N, and the like.

Figure 9:
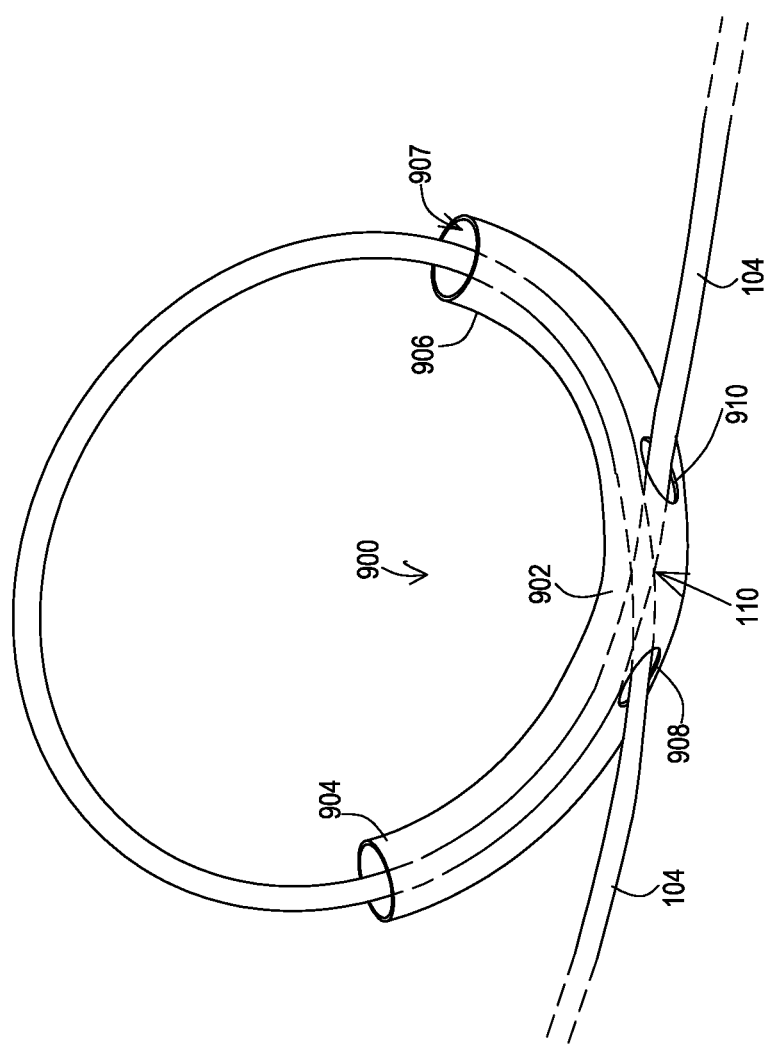
FIG. 9 shows a fourth example of a medial lead strain relief system including a tenth example of a strain relief loop holder that is a continuous tube with intermediate apertures.

FIG. 9 shows another example of a strain relief loop holder 900 that may be used in the system of FIG. 1. This strain relief loop holder 900 is a continuous tube with a center section 902 and end sections 904, 906 together defining a lead passageway 907. The intersection point of the medical lead 104 occurs within the center section 902 and therefore the center section 902 may have a larger diameter than the end sections 904 906. The center section 902 may also define apertures 908 and 910 that provide an entry to allow the medical lead 104 to enter and exit the strain relief loop holder. This example may be constructed of thermal non-conductors or thermal conductors. Furthermore, in the case of thermal non-conductor construction, a dopant or metal insert may be included as discussed above in relation to FIGS. 4 and 7.

Figure 10:
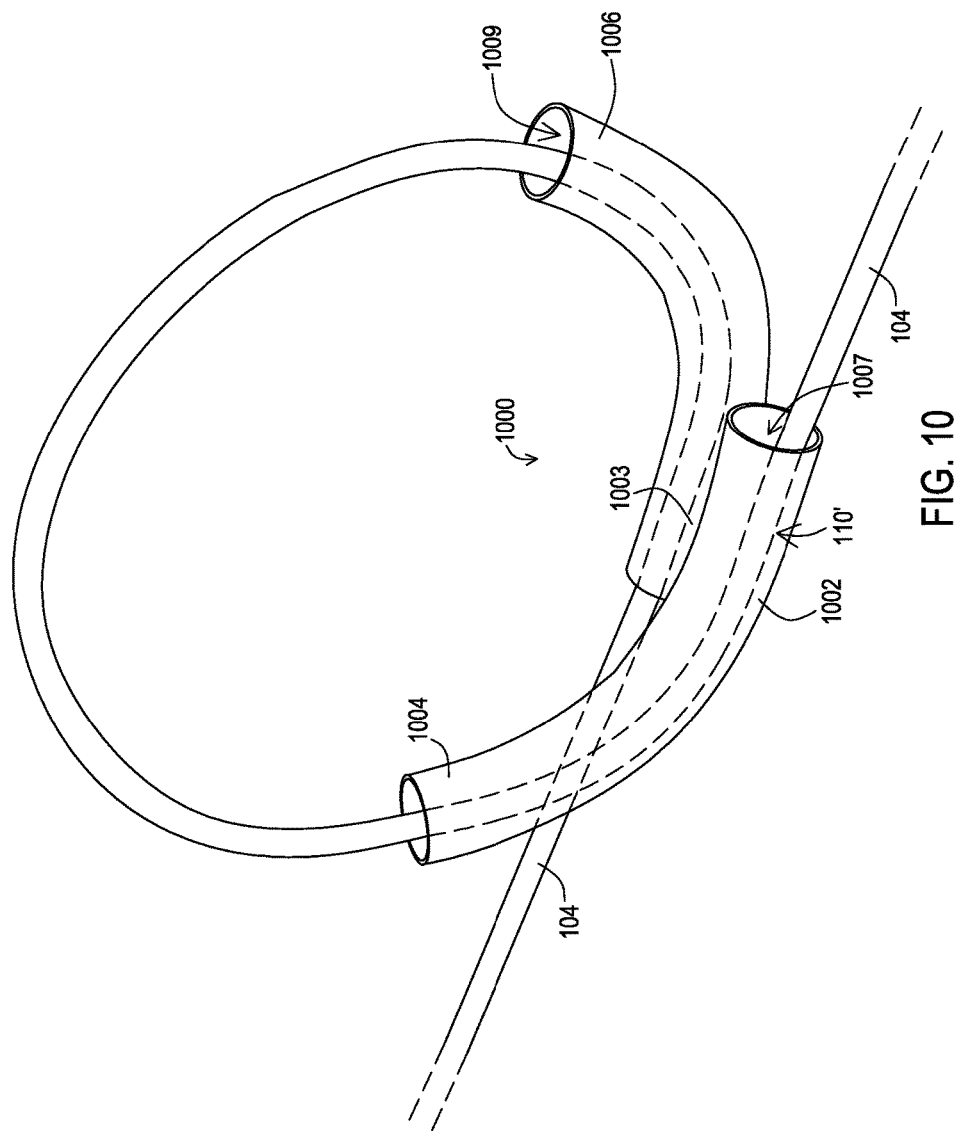
FIG. 10 shows a fifth example of a medical lead strain relief system including an eleventh example of a strain relief loop holder that is a pair of conjoined continuous tubes.

FIG. 10 shows another example of a strain relief loop holder 1000 that may be used in the system of FIG. 1. The strain relief loop holder 1000 utilizes continuous conjoined tubes forming center sections 1002 and 1003 and end sections 1004 and 1006 defining lead passageways 1004, 1009, respectively. In this case, each tube contains a single pass of the medical lead 104 and therefore both the center sections 1002, 1003 and the end sections 1004, 1006 are the same diameter in this example. This example may also be constructed of thermal non-conductors or thermal conductors. Furthermore, in the case of thermal non-conductor construction, a dopant, metal insert, or metal body may be included as discussed above in relation to FIGS. 4, 7, and 8.

Figure 11:
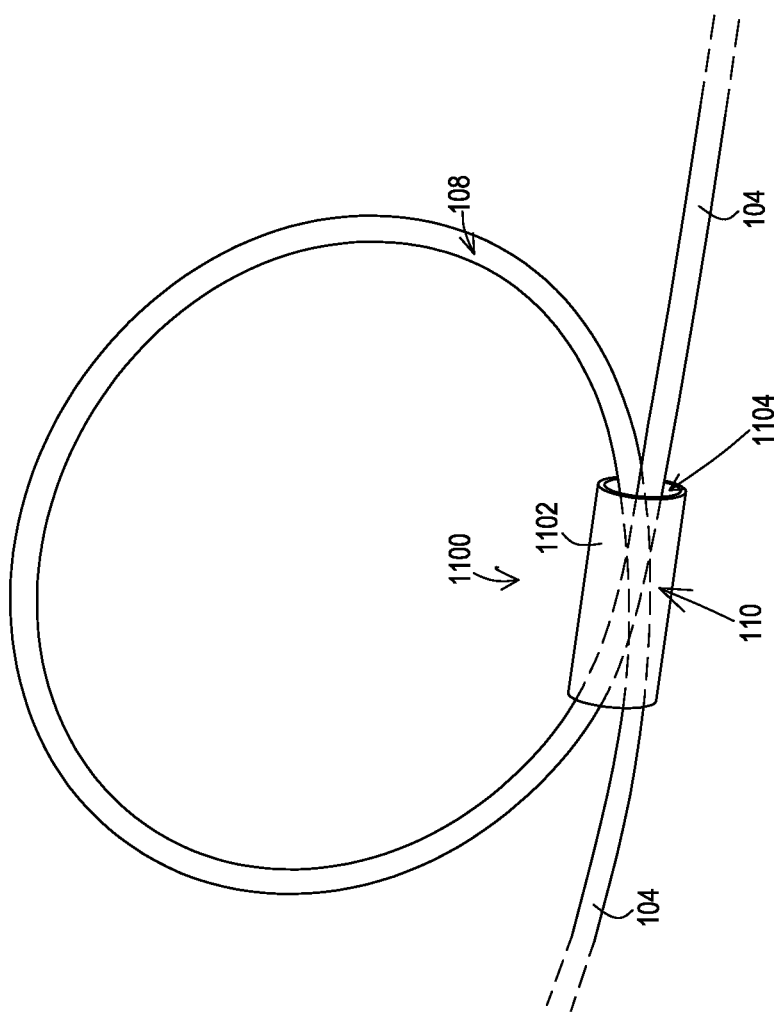
FIG. 11 shows a sixth example of a medical lead strain relief system including a twelfth example of a strain relief loop holder.

FIG. 11 shows another example of a strain relief loop holder 1100 that may be used in the system of FIG. 1 and that utilizes a body 1102 with a single tube. In this case, the tube 1102 defines a lead passageway 1104. As in the prior examples, the lead 104 passes through the lead passageway 1104 loosely to form the strain relief loop 108 and intersection point 110 where the diameter of the lead passageway 1104 is larger than the lead body 104 to allow unrestricted axial movement of the lead 104 through the passageway 1104. This example may also be constructed of thermal non-conductors or thermal conductors. Furthermore, in the case of thermal non-conductor construction, a dopant, metal insert, or metal body may be included as discussed above in relation to FIGS. 4, 7, and 8.

Figure 12:
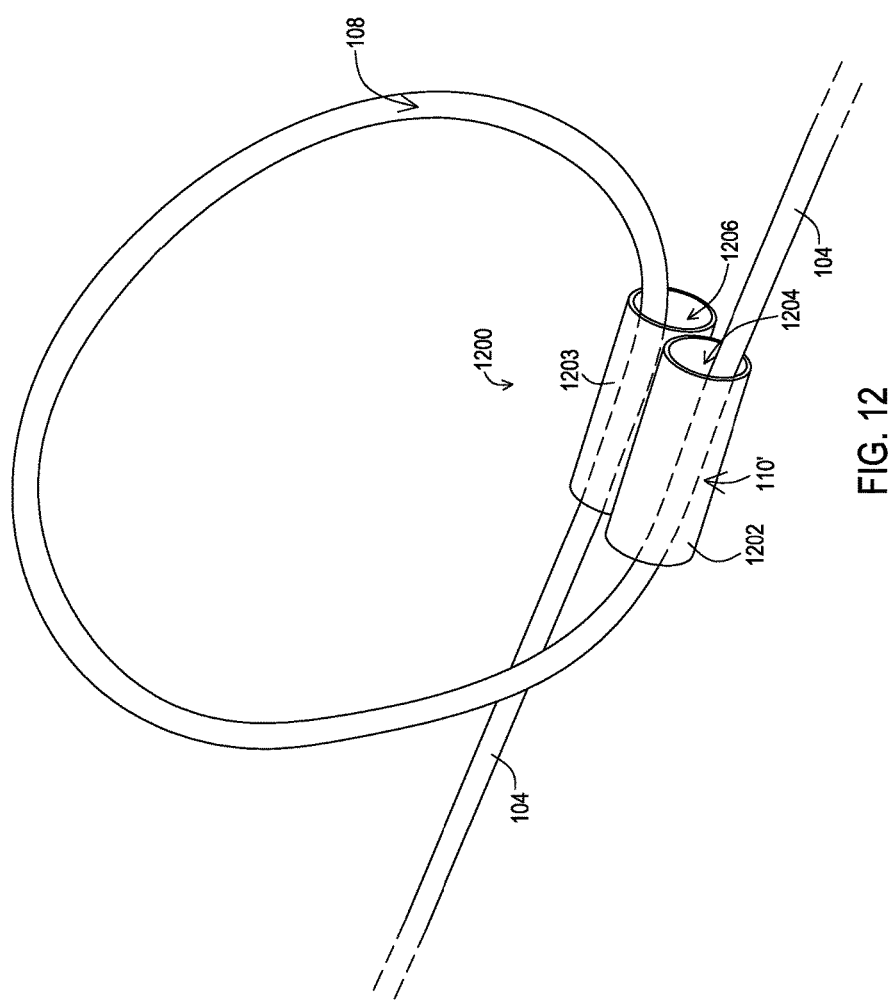
FIG. 12 shows a seventh example of a medical lead strain relief system including a twelfth example of a strain relief loop holder.

FIG. 12 shows another example of a strain relief loop holder 1200 that may be used in the system of FIG. 1 and that utilizes a body 1202 that includes an additional tube 1203 to thereby form two adjacent central sections. In this case, the body 1202 including the additional tube 1203 defines lead passageways 1204 and 1206. As in the prior examples, the lead 104 passes through the lead passageways 1204, 1206 loosely to form the strain relief loop 108 and intersection point 110' where the diameter of the lead passageways 1204, 1206 are larger than the lead body 104 to allow unrestricted axial movement of the lead 104 through the passageways 1204, 1206. This example may also be constructed of thermal non-conductors or thermal conductors. Furthermore, in the case of thermal non-conductor construction, a dopant, metal insert, or metal body may be included as discussed above in relation to FIGS. 4, 7, and 8.

Figure 13:
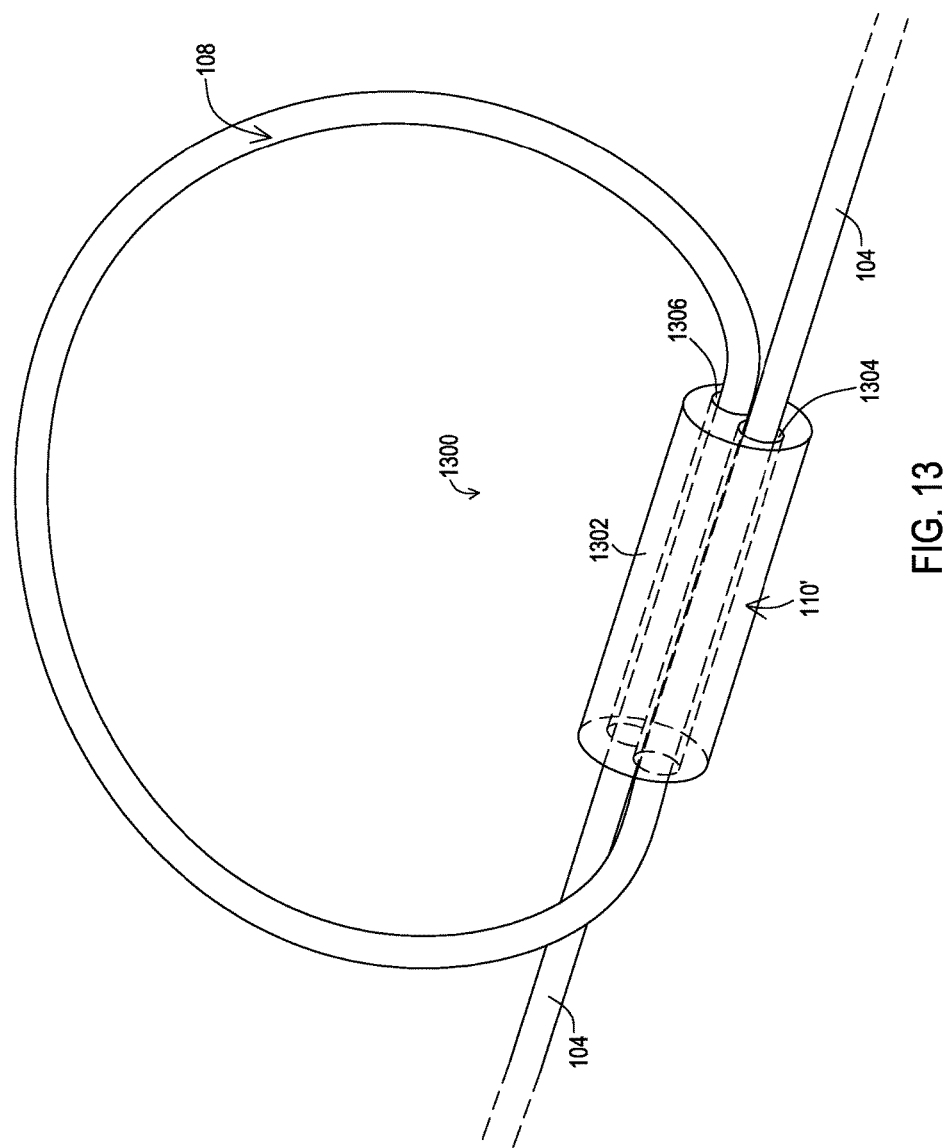
FIG. 13 shows an eighth example of a medical lead strain relief system including a thirteenth example of a strain relief loop holder.

FIG. 13 shows another example of a strain relief loop holder 1300 that may be used in the system of FIG. 1 and that utilizes a body 1302 with a single tubular central section that defines two lead passageways 1304, 1306. As in the prior examples, the lead 104 passes through the lead passageways 1304, 1306 loosely to form the strain relief loop 108 where the diameter of the lead passageways 1304, 1306 is larger than the lead body 104 to allow unrestricted axial movement of the lead 104 through the passageways 1304, 1306. This example may also be constructed of thermal non-conductors or thermal conductors. Furthermore, in the case of thermal non-conductor construction, a dopant, metal insert, or metal body may be included as discussed above in relation to FIGS. 4, 7, and 8.

Figure 14:
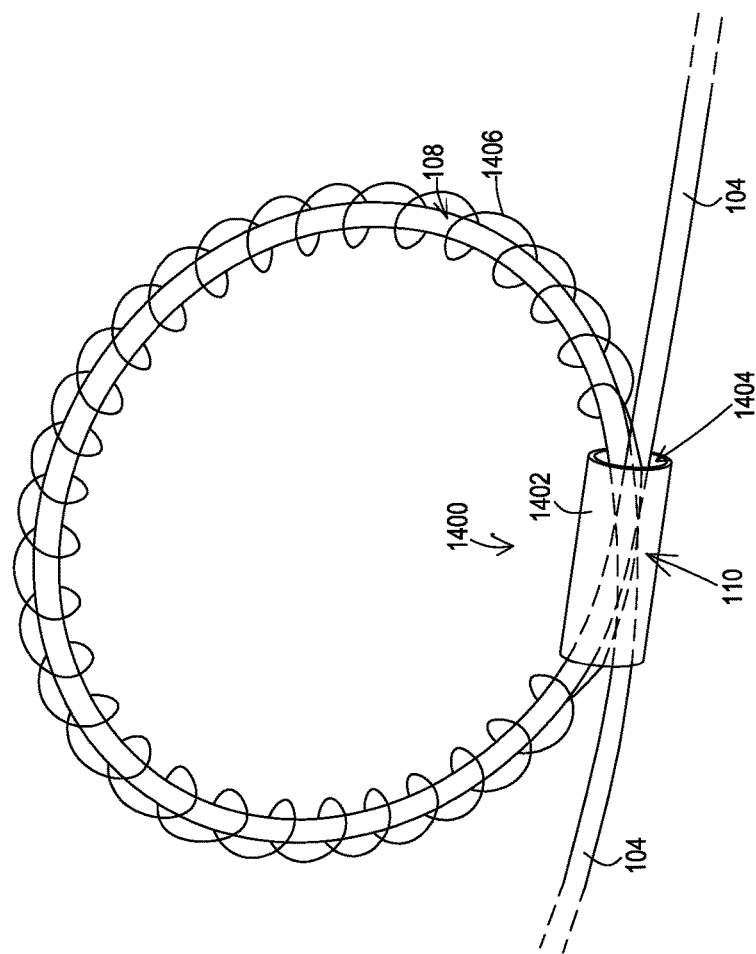
FIG. 14 shows a ninth example of a medical lead strain relief system including a fourteenth example of a strain relief loop holder.

FIG. 14 shows another example of a strain relief loop holder 1400 that may be used in the system of FIG. 1. The strain relief loop holder 1400 utilizes a body 1402 with a single tube to define a lead passageway 1404 at the intersection point 110 but also utilizes a looped coil 1406. As in the prior examples, the lead 104 passes through the lead passageway 1404 loosely to form the strain relief loop 108 where the diameter of the lead passageway 1404 is larger than the lead body 104 to allow unrestricted axial movement of the lead 104 through the passageway 1404. The loop 108 is constrained to a particular shape and size by the presence of the looped coil 1406 which is coupled to the body 1402. The looped coil 1406 may be constructed of non-conductive materials such as polyurethane, silicone, or conductive materials that have a non-conductive coating such as ETFE coated titanium, titanium molybdenum, or MP35N. This example may also be constructed of thermal non-conductors or thermal conductors. Furthermore, in the case of thermal non-conductor construction, a dopant, metal insert, or metal body may be included as discussed above in relation to FIGS. 4, 7, and 8.

Figure 15:
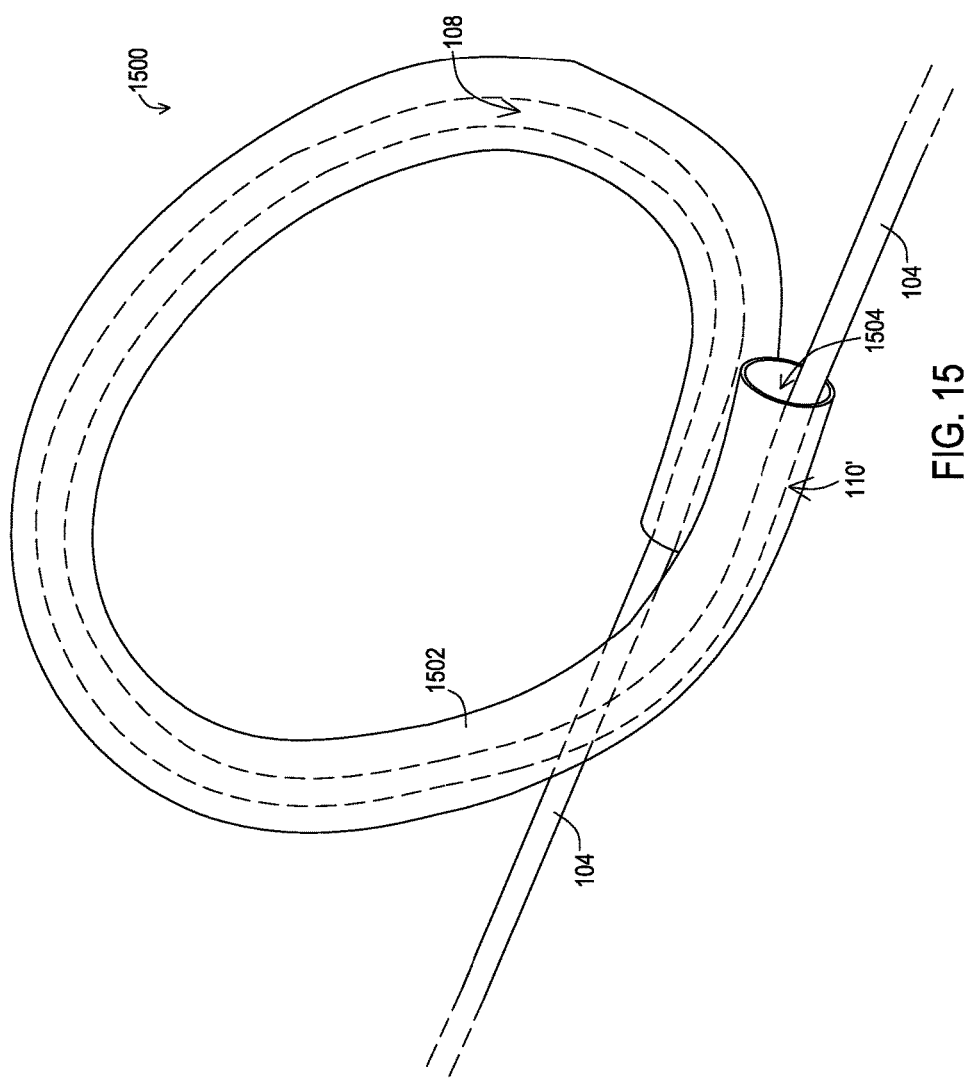
FIG. 15 shows a tenth example of a medical lead strain relief system including a fifteenth example of a strain relief loop holder.

FIG. 15 shows another example of a strain relief loop holder 1500 that may be used in the system of FIG. 1 and that utilizes a body 1502 that provides a single tube. In this case, the body 1502 defines a lead passageway 1504. Additionally, the body 1502 is also looped. As in the prior examples, the lead 104 passes through the lead passageway 1504 loosely with the lead passageway 1504 to form the strain relief loop 108 where the diameter of the lead passageway 1504 is larger than the lead body 104 to allow unrestricted axial movement of the lead 104 through the passageway 1504. The looped shape of the body 1502 constrains the shape and size of the loop 108 of the lead 104. This example may also be constructed of thermal non-conductors or thermal conductors. Furthermore, in the case of thermal non-conductor construction, a dopant, metal insert, or metal body may be included as discussed above in relation to FIGS. 4, 7, and 8.

Figure 16:
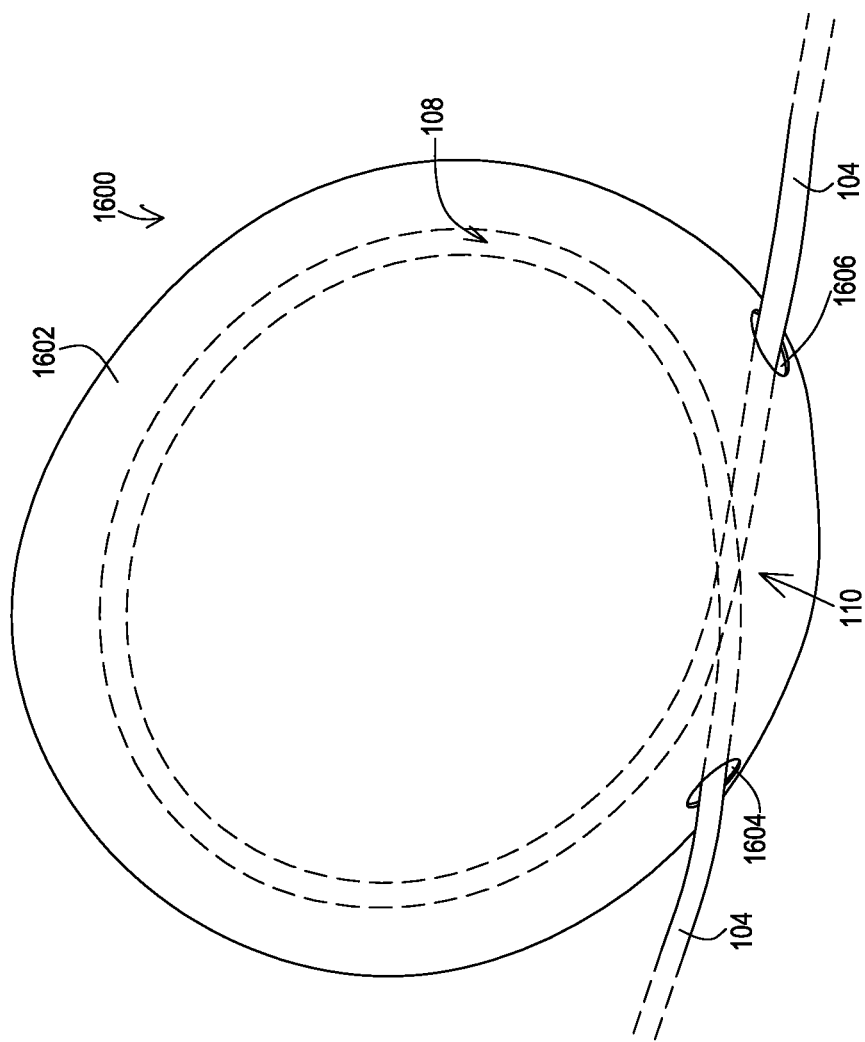
FIG. 16 shows an eleventh example of a medical lead strain relief system including a sixteenth example of a strain relief loop holder.

FIG. 16 shows another example of a strain relief loop holder 1600 that may be used in the system of FIG. 1. The strain relief loop holder 1600 utilizes a body 1602 that forms a capsule to completely house the loop 108 of the lead 104 such that the passageway for the lead 104 is the entire internal volume of the strain relief loop holder 1600. The lead enters and exits the body 1602 through apertures 1604 and 1606 forming an entry to the interior volume of the body 1602. This example may also be constructed of thermal non-conductors or thermal conductors. Furthermore, in the case of thermal non-conductor construction, a dopant, metal insert, or metal body may be included as discussed above in relation to FIGS. 4, 7, and 8.

In each of the examples of the strain relief loop holder, the lead body 104 could be affixed to one side of the holder so that the holder and the lead 104 are inseparable. In this case, the strain relief holder is already present on the lead 104 at the time of implant so that the holder is not inadvertently or intentionally omitted during the implantation procedure. By affixing one side of the older to the lead, the strain relief function is preserved. For example, both leads 104, 105 may be affixed to the arm section 310 such as by a bond created by an adhesive or by melding the lead body to the arm section by reflowing the polymers of the two at that point.

While embodiments have been particularly shown and described, it will be understood by those skilled in the art that various other changes in the form and details may be made therein without departing from the spirit and scope of the invention.

What is claimed is:

1. A method of providing strain relief for an implantable medical lead, comprising:
    providing a strain relief loop holder comprising a body segment defining at least one passageway with a first opening of the at least one passageway on a first end of the body segment and a second opening of the at least one passageway on a second end of the body segment, a first arm extending from the first end of the body segment, a first arm segment at an end of the first arm opposite the body segment, the first arm segment defining a first arm passageway, a second arm extending from the second end of the body segment, and a second arm segment at the end of the second arm opposite the body segment, the second arm segment defining a second arm passageway; and
    passing the lead through the passageway of the body segment in a first direction and through the first arm passageway such that a first portion of the lead exits the first arm passageway while a second portion extends from the passageway in a direction opposite from the first arm segment;
    forming the first portion of the lead that exits the first arm passageway into a loop;
    passing a first sub-portion of the first portion through the second arm passageway and through the passageway of the body segment in a second direction that is opposite the first direction to create an intersection of the lead within the body segment.

2. The method of claim 1, wherein the first arm and second arm have an arc shape.

3. The method of claim 1, wherein the body segment defines a single passageway and wherein both the first arm and the second arm extend from the single passageway.

4. The method of claim 1, wherein the body segment defines a first passageway and a second passageway, wherein the first arm extends from the first passageway, and wherein the second arm extends from the second passageway.

5. The method of claim 4, further comprising a metal body between the first and second passageways.

6. The method of claim 1, wherein the body segment, first arm, and second arm are constructed of a polymer.

7. The method of claim 6, wherein the body segment is doped with a conductive material.

8. The method of claim 6, further comprising a metal insert within the body segment.

9. The method of claim 1, wherein the body segment, first arm, and second arm are constructed of a metal.

10. The method of claim 1, wherein the strain relief loop holder further comprises an anchor tab extending from the body segment.

11. The method of claim 1, wherein the at least one body segment passageway has a diameter greater than a diameter of the first arm passageway and second arm passageway.

12. A method of providing strain relief for an implantable medical lead, comprising:
    providing a strain relief loop holder comprising a body segment defining at least one passageway, a first arm extending from the first end of the body segment, a first arm segment at an end of the first arm opposite the body segment, the first arm segment defining a first arm passageway, a second arm extending from the second end of the body segment, and a second arm segment at the end of the second arm opposite the body segment, the second arm segment defining a second arm passageway; and
    passing a medical lead through the first arm passageway and the second arm passageway, the medical lead forming a loop by passing through and intersecting within the body segment.

13. The method of claim 12, wherein the first arm and second arm have an arc shape.

14. The method of claim 12, wherein the body segment defines a single passageway, wherein both the first arm and the second arm extend from the single passageway, and wherein the medical lead intersects within the single passageway.

15. The method of claim 12, wherein the body segment defines a first passageway adjacent to a second passageway, wherein the first arm extends from the first passageway, and wherein the second arm extends from the second passageway, and wherein the medical lead intersects within the body segment by passing through both the first and second passageways.

16. The method of claim 12, wherein the body segment, first arm, and second arm are constructed of a polymer.

17. The method of claim 16, wherein the body segment is doped with a conductive material.

18. The method of claim 12, wherein the body segment, first arm, and second arm are constructed of a metal.

19. The method of claim 12, further comprising an anchor tab extending from the body segment.

20. The method of claim 12, wherein the at least one body segment passageway has a diameter greater than a diameter of the first arm passageway and second arm passageway.

* * * * *